United States Patent [19]
Stein

[11] Patent Number: 5,425,870
[45] Date of Patent: Jun. 20, 1995

[54] MULTIPURPOSE ELECTROLYTIC METER

[76] Inventor: Berl Stein, 43 Beauvoir Ave., Summit, N.J. 07901

[21] Appl. No.: 138,501

[22] Filed: Oct. 19, 1993

[51] Int. Cl.$^6$ ............................................. G01N 27/26
[52] U.S. Cl. ................... 204/434; 204/400; 204/412
[58] Field of Search ................ 204/400, 434, 404, 412

[56] References Cited

U.S. PATENT DOCUMENTS

| | | | |
|---|---|---|---|
| 2,947,679 | 8/1960 | Schaschl et al. | 204/404 |
| 3,067,123 | 12/1962 | Huber | 204/434 |
| 3,121,053 | 2/1964 | Hull et al. | 204/434 |
| 3,504,323 | 3/1970 | Meany | 204/404 |
| 3,925,168 | 12/1975 | Costas | 204/434 |
| 4,096,051 | 6/1978 | Annis et al. | 204/196 |
| 4,233,031 | 11/1980 | Matson et al. | 204/412 |
| 4,932,518 | 6/1990 | Bernards et al. | 204/52.1 |
| 5,236,571 | 8/1993 | Blechta et al. | 204/434 |
| 5,252,192 | 10/1993 | Ludwig | 204/434 |

OTHER PUBLICATIONS

Von J. Heyes, "Das Elektrolytische Polieten von . . . ", p. B184. 1961.
D. A. Luke, "Notes on Throwing Power Measurement". 1982.
S. Shawki et al. "Throwing Power". 1987.

Primary Examiner—T. Tung

[57] ABSTRACT

An instrument for measuring the throwing power, electrochemical efficiency and operating current density of an electrolyte comprises a number of removable electrodes (20) arranged inside a nonconductive probe body (10) with an open end (11) and an optional solution circulation opening at its opposite end (30) with the electrodes connected via current meters (80) to a current controller (70).

5 Claims, 4 Drawing Sheets

MULTIPURPOSE ELECTROLYTIC METER

BACKGROUND OF THE INVENTION

1. Field of the Invention

This invention is in the field of electrolytic processing of materials and measurement of electrolyte parameters. More particularly, the present invention is in the field of methods for measuring characteristics of electrolytic processing, including, e.g., uniformity, or throwing power; electrochemical efficiency; and operating current density range.

2. Description of the Prior Art

Throwing power, electrochemical efficiency and the operating current density range are important characteristics of a processing electrolyte and, consequently, the process itself. They determine the uniformity of electrochemical action over articles of irregular shape—the distribution of plating thickness in the case of electrodeposition or the amount of metal removed in an anodic process. Throwing power is generally understood as the ability of an electrolyte to deposit metal cathodically in narrow recesses and small-diameter holes, or, conversely, to dissolve metal from shielded areas anodically. Electrochemical efficiency determines the actual amount of deposited or dissolved metal based on the amount of electricity used in the process. It often varies with the local current density and is a function of electrolyte composition. The variation of current density over the surface of an object undergoing electrochemical processing is known as the secondary current distribution; see *Electroplating Engineering Handbook*, ed. by L. Durney, Van Nostrand Reinhold Co., 1984, p. 461–469. Secondary current distribution is determined by polarization and other electrochemical effects modifying the primary current distribution, which is the ideal or theoretical current distribution in the absence of secondary effects. The operating current density range defines the upper and lower limits of current density for a given process, below and above which no acceptable results can be obtained.

The ability to quickly and accurately measure these parameters would provide the means for maintaining a processing electrolyte in optimum condition and evaluate effects that additives, impurities and changes in operating conditions have on the process performance.

Traditional methods for measuring throwing power, operating current density range and electrochemical efficiency of electrolytes are described in part by D. A. Luke in "Notes on Throwing Power Measurement", *Transactions of the Institute of Metal Finishing*, v. 61, 1983, p. 64–66, and Von J. Heyes in "Das elektrolytische Polieren von Stahl mit einem uberchlorsaurehaltigen Elektrolyten", *Metalloberflache*, N. 12, 1961, p. B181-B190. Such methods of the prior art require that a sample of electrolyte be tested in a plating cell such as the Haring or the Hull cell, both well known in the art.

To conduct a test such as those which utilize plating from a Haring or Hull cell, a sample of the solution is transferred to the appropriate cell, furnished with a power source, an anode and a cathode panel. Electrolysis is then carried out in the cell for a predetermined amount of time at the appropriate current level. Thereafter, the amount of deposited or dissolved metal (depending on the nature of the process) on different sections of the anode or the cathode panel is determined and used to calculate the throwing power, electrochemical efficiency and operating current density for the tested electrolyte.

There are no universally accepted units for the expression of throwing power. Often, the weight ratio of metal deposits formed at particular high and low current density areas of the cathode panel is used to express the throwing power of a plating bath.

In addition to their main disadvantage, i.e., the impossibility of measuring electrolyte properties directly in process tanks using existing counterelectrodes and current sources, traditional methods are cumbersome, time-consuming and, as pointed out by Luke, very sensitive to the electrolytic cell arrangement, especially the cathode-to-anode distance and relative position. Because of difficulties with the interpretation of test results, also discussed by Luke, traditional test methods have little predictive value. Consequently, the industry relies on a variety of tests involving the processing of an actual object of interest, such as, e.g. plating into a small-diameter hole (via) in a printed circuit board, and measuring the metal distribution over that object destructively to evaluate the throwing power of electrolytes. One such test was described by S. Shawki et al. in "Throwing Power", *Metal Finishing*, p. 59–61, December 1987. This approach is even more time-consuming and expensive than methods involving plating cells. Its use for routine process maintenance is, therefore, very limited.

More recently, R. F. Bernards et al. made an attempt to overcome difficulties associated with the described traditional approaches by proposing a method and apparatus for in-tank throwing power determination in U.S. Pat. No. 4,932,518 (1990). Their method involves two cathode assemblies, each consisting of one center, two edge and two surface electrodes, arranged parallel to each other and spaced apart in a plating tank. An additional thieving cathode is used to improve the plating uniformity over the parallel cathodes. A pair of anodes is suspended perpendicular to the cathode assemblies on both sides of them, with the assemblies centered between the two anodes. Throwing power in this method is expressed as the current ratio between the edge and center electrode portions of the cathode assemblies during electroplating.

This method, while allowing for tests to be carried out directly in a plating tank, has nevertheless not become a widely used or accepted testing procedure. Test results are, as in the previously described classical methods, dependent on the anode-to-cathode distance and relative position. Moreover, the distance between the two halves of the cathode assembly has an additional bearing on the results. To express throwing power as the current ratio is to assume that electrochemical efficiency is independent of the current density, which in general is not true. Indeed, it is well known in the art that many electrochemical systems rely on reduced efficiency at higher current densities (caused by polarization and other effects) for improved throwing power.

Solution agitation is an important process variable, but neither of the methods discussed above is capable of measuring its effects on throwing power quantitatively. Agitation, which has a strong influence on the processing uniformity, can only be quantified if provisions are made for accurate solution circulation rate measurement. None of the discussed methods makes such provisions or can be easily adopted for that purpose.

Summarizing, it can be said that the best known to date method for in-tank measurement of throwing power according to U.S. Pat. No. 4,932,518 is very complicated, requiring a total of eleven cathode and two anode electrodes to be arranged a certain way in a plating tank, sensitive to the anode-to-cathode distance and relative position, and limited in scope. Only allowing measurement of what is known in the art as the secondary current distribution for a particular cell arrangement, the method taught in the U.S. Pat. No. 4,932,518 does not allow determination of the true electrolyte processing uniformity. The method can not be used to determine the electrochemical efficiency of a process, without which throwing power can not be established based on the current ratio alone. Further, that method does not provide quantitative assessment of agitation effects on throwing power, nor does it predict the processing uniformity for actual objects, such as, e.g., blind vias in printed circuit boards.

OBJECTS AND ADVANTAGES

Accordingly, several objects of my invention, providing it with advantages over the prior art, are to provide a method and apparatus:

a) for measuring simultaneously the secondary current distribution, electrochemical efficiency, throwing power and operating current density range of an electrochemical process;

b) directly useful in a process tank with existing counterelectrodes and power sources, under the actual processing conditions rather than in a simulated plating cell environment, thereby significantly speeding up the testing and improving its accuracy;

c) whose measurements will not be influenced by the position and attitude of the sensor in the solution;

d) with high predictive value so that test results can be used to prognosticate the processing uniformity on actual articles;

e) which permits measurement of what effects agitation, as well as other process variables, have on throwing power, electrochemical efficiency and operating current density range; and f) which is relatively simple, consisting of a small number of elements, for the realization of enumerated objects.

Further objects and advantages will become apparent from a consideration of the ensuring description and drawings.

SUMMARY OF THE INVENTION

The present invention is a method and apparatus for measuring the operating characteristics of an electrochemical processing solution, the apparatus comprising a plurality of small electrodes, means for delivering current to the electrodes, and means for measuring the currents flowing to each of the electrodes separately. At least one nonconductive rigid enclosure, large enough to accommodate the electrodes, is provided with at least one opening, the electrodes being mounted inside the enclosure at various distances from the enclosure opening, thereby providing the ability to measure, e.g., throwing power and operating current density range of the processing solution simultaneously directly in a process tank using an existing counterelectrode and current source, substantially independently of the position of the enclosure having the electrodes mounted inside it in the process tank during the measurements.

The method of this invention comprises the use of the apparatus described herein to determine the operating parameters of an electrolytic bath, and using those parameters to observe and control the functions of the bath during production runs.

DESCRIPTION OF THE PREFERRED EMBODIMENTS

Figure 1:
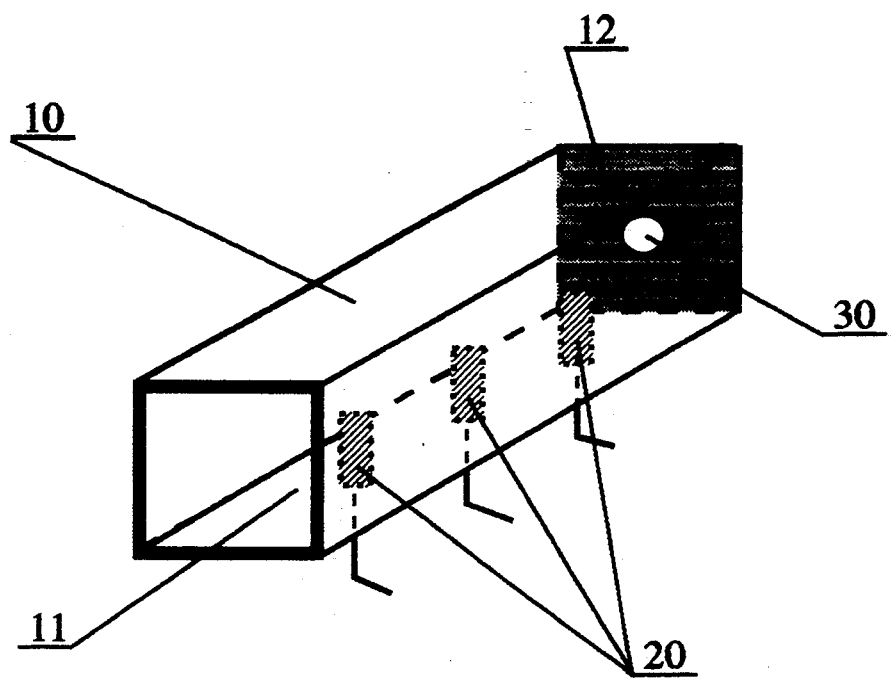
FIG. 1 is a perspective view of one embodiment of the probe of my multipurpose electrolytic meter.

The main element of my multipurpose electrolytic meter is its probe, an embodiment of which is shown in FIG. 1. The probe body 10 is an elongated, hollow object made of a nonconductive, chemically inert, preferably rigid material. Examples of materials useful for this purpose include plastics such as, e.g., polyethylene, polypropylene, polyvinyl chloride, polycarbonates, phenol-formaldehydes and the like, glass, and wood. Transparent plastics or glass would facilitate the visual inspection of the surface of the electrodes; therefore, their use for the probe body is highly desirable. It is within the spirit and scope of this invention to use metal for the probe body, provided that the metal is so coated with an inert material as to preclude any interaction with electrolytic current.

One end of the probe cavity 11 is open while the opposite end 12 is closed. The closed end of the probe body may be provided with an optional aperture 30 for forced solution circulation. The shape of the cross-section of the probe cavity has no particular importance and can be chosen arbitrarily as round, rectangular or otherwise. The probe is preferably provided with a handle or clamp (not shown) for positioning it in the solution during measurements or for otherwise moving it.

Inside the body 10 of the probe are located a plurality of removable conductive electrodes 20. The electrodes can be made removable by conventional means well known to those skilled in the art, and forming no part of this invention as such. Such means include, e.g., threaded connectors or various quick-release joints (not shown in the drawings). Metals such as, e.g., carbon steel, stainless steel, and alloys of copper and nickel, are suitable electrode materials. In the method of this invention, a particular metal is preferably chosen in accordance with the application. For anodic processes, the electrodes should be made from the same metal as the actual parts undergoing processing. For cathodic processes, the electrode material should be easy to activate and to plate upon, and one from which the electrodeposit is easily stripped such that the electrodes are reusable.

Figure 2:
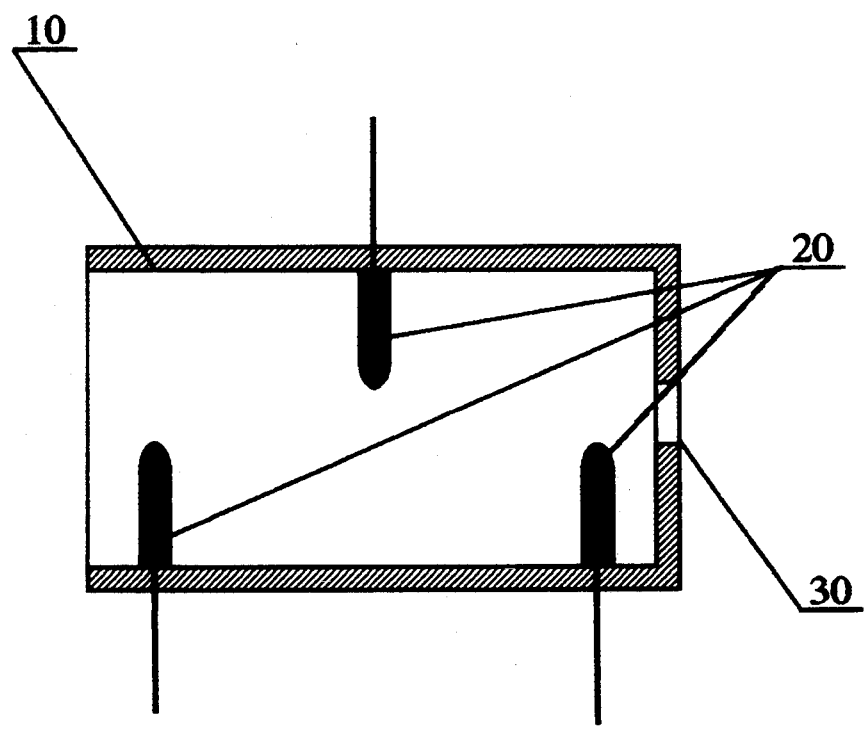
FIG. 2 is a cross-sectional view of another embodiment of the probe of this invention.
Figure 3:
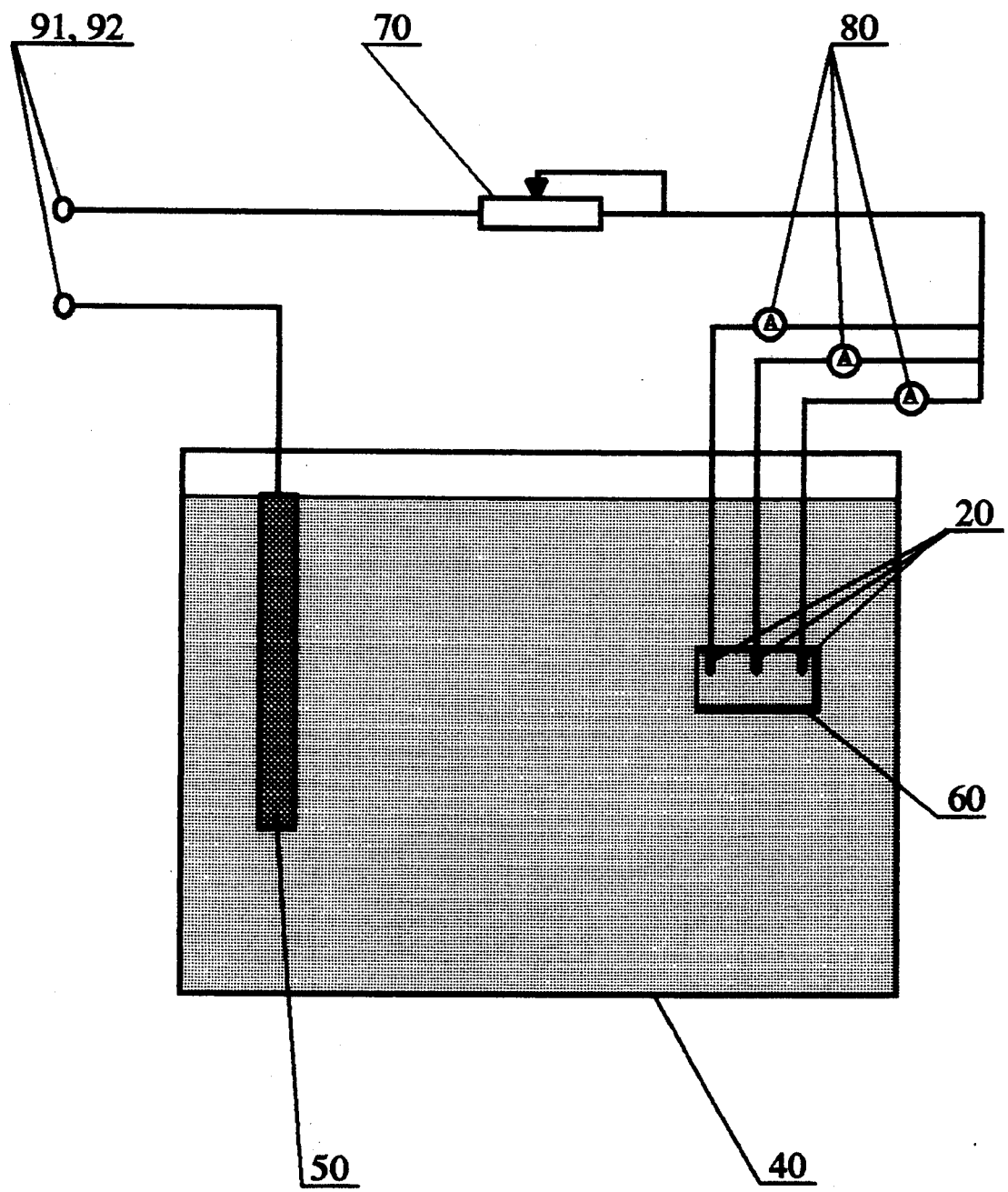
FIG. 3 is a schematic diagram showing the principle of throwing power measurement with my meter.

While in FIGS. 1, 2 and 3 there are shown three-electrode probe versions, a probe can have as few as two or as many electrodes as practically possible and necessary for a particular application. Irrespective of the number of electrodes, each one is provided with a separate insulated wire lead connecting it to a current measuring device. The electrodes inside the probe are placed at various distances from its open end 11. The shape of the electrodes is not critical as long as their cross-sectional area is substantially smaller than that of the probe opening. Although not mandatory, the electrodes should preferably be made substantially identical in size and shape. The electrodes can be arranged in the probe cavity in a straight line as shown in FIG. 1, or staggered as shown in FIG. 2. Those skilled in the art will realize that other electrode arrangements, although not shown here, are possible.

As shown in FIG. 3, the apparatus of this invention further contains current meters 80. Their number is equal to the number of electrodes 20 in the probe 60. As can be seen from the drawing, each probe electrode is connected by its lead to a separate current meter. The opposite current meter leads are joined together and connected to a current controller 70. The current controller is connected to the corresponding pole 91 or 92 of the power source, positive for an anodic process or negative for a cathodic one. During measurements the probe is immersed in a process tank 40, containing an electrolyte and a counterelectrode 50. Completing the circuit, the counterelectrode is connected to the opposite pole of the power source 92 or 91.

OPERATION OF THE METER a) Basic Principles

As described hereinabove, a secondary current distribution is established on the surface of any article subjected to electrochemical action in an electrolyte, the distribution reflecting the geometry of the article-counterelectrode arrangement and the properties of the electrolyte. That current distribution combined with local electrochemical efficiencies determines the overall processing uniformity, or throwing power.

In the operation of the invention, a hollow elongated nonconductive object has a number of relatively small electrodes arranged inside it at various distances from the single cavity opening, the electrodes being in electrical contact with each other. When subjected to electrochemical action in an electrolyte, different currents are established on different electrodes, depending on each electrode's distance from the opening, and the electrolyte properties. These currents will constitute the secondary current distribution for that particular object.

It has been shown in my tests that the secondary current distribution over an object of the described geometry is not influenced by its position or distance relative to one or more counterelectrodes in a process tank. This fact forms the basis of my measurement system, which is independent of the electrochemical cell geometry and the distance from the counterelectrode. It may be explained by some published mathematical simulation results, according to which an opening in a nonconductive object separating oppositely charged electrodes in an electrolyte is electrochemically equivalent to a counterelectrode located in its place.

The actual metal distribution over the probe electrodes can be calculated based on the measured secondary current distribution and the electrochemical efficiency using formula A, $$M = I*t*E*\eta.$$

where M is the mass of the deposited or dissolved metal, I—current, t—time, E—the electrochemical equivalent of the metal, and $\eta$—electrochemical efficiency. However, that could not be done without prior knowledge of the efficiency $\eta$.

Using the instrument of this invention, the electrochemical efficiency can be established as a function of current density, which allows determination of the metal distribution and the true throwing power of the process. To measure the electromechanical efficiency, the probe electrodes 20 (FIGS. 1 and 2) of a known exposed surface area (area open to processing) are prepared by conventional cleaning and activating, and are weighed and mounted in the probe body 10. The probe is immersed in a process tank 50, the test circuit according to FIG. 3 is assembled and connected to the power source outputs 91 and 92, with the desired total probe current selected by use of the controller 70. The secondary current distribution is registered by meters 80. Because the electrodes are small in size, the current density over each of them does not vary substantially. Therefore, the local current density for every electrode can be calculated as the ratio of current flowing through the electrode to its exposed surface area. After a desired amount of time has passed, the current is turned off, and the electrodes are rinsed and removed from the probe. They are weighed again and their weight loss or gain M is calculated. Substituting into Formula A the values of M, I and t obtained in the test, and the known value of E, the electrochemical efficiency $\eta$ is calculated for each electrode separately.

Thus, in one test for each electrode of the probe, a pair of related values, i.e., the local current density and the corresponding electrochemical efficiency, are established. By repeating the test at various currents, a wide current density range can be covered, resulting in an electrochemical efficiency vs. current density relationship, characteristic of a given electrolyte. That relationship can be used in subsequent tests to calculate the metal distribution (true throwing power) based on secondary current distribution readings only, without having to repeat the efficiency measurements. The described approach makes routine electrolyte maintenance quick and straightforward. Once the influence of current density on throwing power has been established in preliminary tests, a simple secondary current distribution measurement provides all the necessary information for throwing power calculation.

As noted hereinbefore, there is no universal expression for throwing power, therefore any convenient formula can be used for this parameter with the method and apparatus of this invention. For a two-electrode probe, for instance, the ratio of metal deposition or dissolution rates on the two probe electrodes can be used. The secondary current distribution over the probe electrodes can also be used if the limitations of that approach, described earlier, are taken into account.

b) Practical Measurements

Based on the described principles, several different modes of operation of the electrolytic meter are set forth here.

To establish the relationship between electrochemical efficiency and current density for a given electrolyte the following sequence of operations can be used:
(a) clean and activate probe electrodes of a known surface area;
(b) weigh the cleaned electrodes;
(c) mount the electrodes in the probe;
(d) immerse the probe into the solution;
(e) turn on the current and a timing device;
(f) record the currents for each electrode;
(g) turn off the current and record the test duration;
(h) rinse and remove the electrodes from the probe; and
(i) weigh the electrodes.

Calculate the weight gain or loss of the electrodes and electrochemical efficiency using Formula A and corresponding current density.

Repeat the test at various currents as many times as is necessary to cover the operating current density range and establish the relationship between electrochemical efficiency and current density. The operating current density range can be established by visually inspecting the electrodes after each test and finding the limiting current densities below and above which the processing quality is not acceptable.

Before the electrodes become heavily plated in a cathodic process or eroded in an anodic one, they should be either replaced with new ones (for an anodic process) or the deposit can be stripped off (for a cathodic process). This should be done after each or several tests, depending on the duration of a single test and the amount of metal deposited or dissolved in it.

For routine electrolyte control and maintenance, after the relationship between the electrochemical efficiency and current density for a particular solution has been established, a much quicker test procedure can be used, as set forth here. The electrodes are cleaned and activated without removing them from the probe. The probe is immersed in the solution and the desired current is selected by use of the controller. Thereafter, the secondary current distribution over the probe electrodes is measured and used to calculate throwing power based on the known electrochemical efficiencies according to principles described earlier. After an adjustment to operating conditions is made, the test is repeated to verify the effectiveness of the correction.

Another application of the instrument of this invention is for research purposes, when the influence of a process variable such as, e.g., agitation, temperature, or concentration on processing uniformity is investigated. Agitation effects can be studied with the use of a pump and flowmeter connected by a flexible tube to the probe solution circulation aperture 30 shown in FIGS. 1 and 2. Measurements of the secondary current distribution, electrochemical efficiency and current density are carried out under various solution circulation rates, and its influence on processing uniformity is evaluated. Tests not involving agitation are identical to the ones described previously, except that they are repeated a number of times with varying values of the parameter under investigation in a still solution. For measurements in unagitated solutions, a probe without a circulation aperture is used or the aperture is closed.

Many other applications of my instrument, though not described here, will occur to those skilled in the art.

The operation of the instrument of the present invention is illustrated by the following examples. All measurements were taken in a proprietary bright copper electroplating solution Copper Gleam PCM Plus (Lea Ronal, Inc., Freeport, N.Y.).

Figure 4:
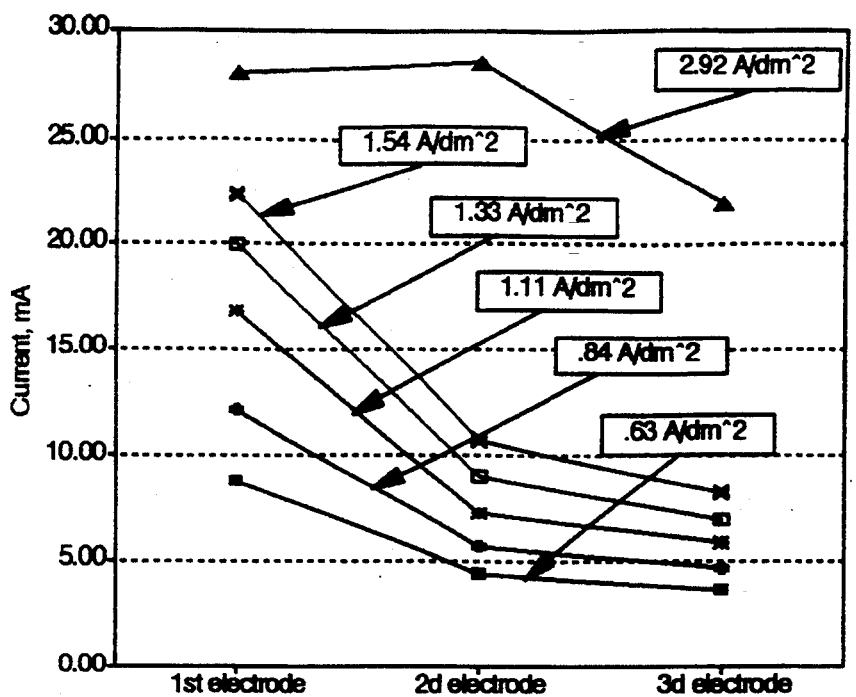
FIG. 4 is a graphic representation of the current distribution over the electrodes of a three-electrode probe of the invention, at various current densities.
Figure 5:
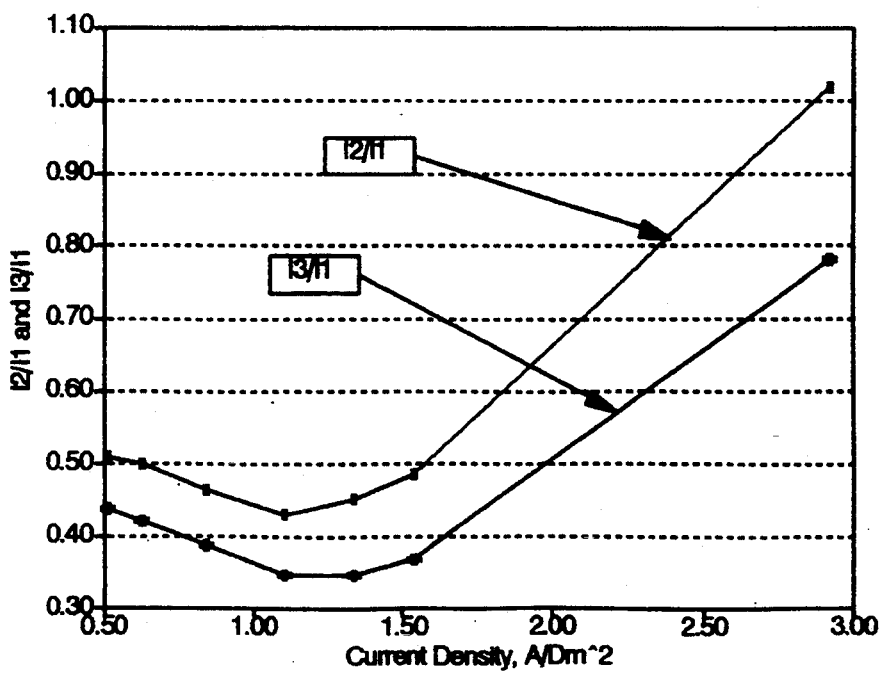
FIG. 5 is a graphic representation of the functional relationship between throwing power, expressed as the ratio of electrode currents, and current density for a three-electrode probe.

In Example 1, tests with a three-electrode probe 60 as shown in FIG. 3 were carried out. Using three identical low-resistance current meters 80, the secondary current distribution over the three electrodes of the probe was measured at different current densities. Results are represented graphically in FIG. 4. Because of the probe geometry, as previously noted, that current distribution, while independent of the probe position in the tank, was a function of process variables such as current density, temperature, agitation, etc. Since the only variable altered in the described test was current density, a relationship between the throwing power expressed as secondary current distribution and current density could be established. In FIG. 5, a graph of this relationship is plotted where $I2/I1$ and $I3/I1$ are, correspondingly, the ratios of the middle electrode to the first electrode and the third electrode to the first electrode currents. It can be seen from this graph, among other things, that both pairs of electrodes reflected the same throwing power variation trend with a minimum at between about 1 and about 1.25 A/dm$^2$ and an increase toward higher current densities. These data support the view that for many applications a two-electrode probe can be quite adequate.

Figure 6:
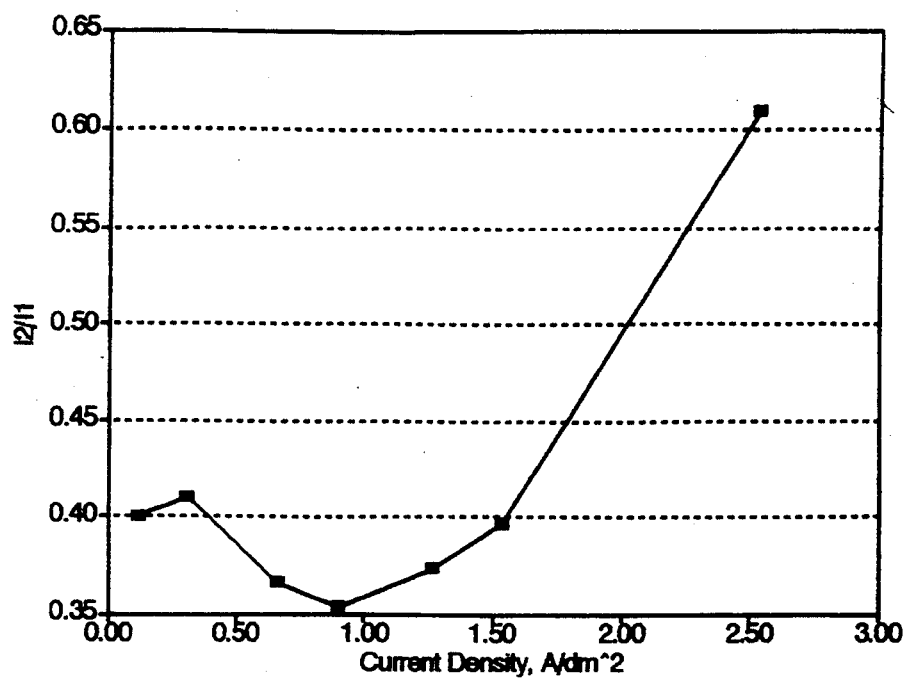
FIG. 6 is a graphic representation of the functional relationship between throwing power, expressed as the ratio of electrode currents, and current density for a two-electrode probe in a still solution.
Figure 7:
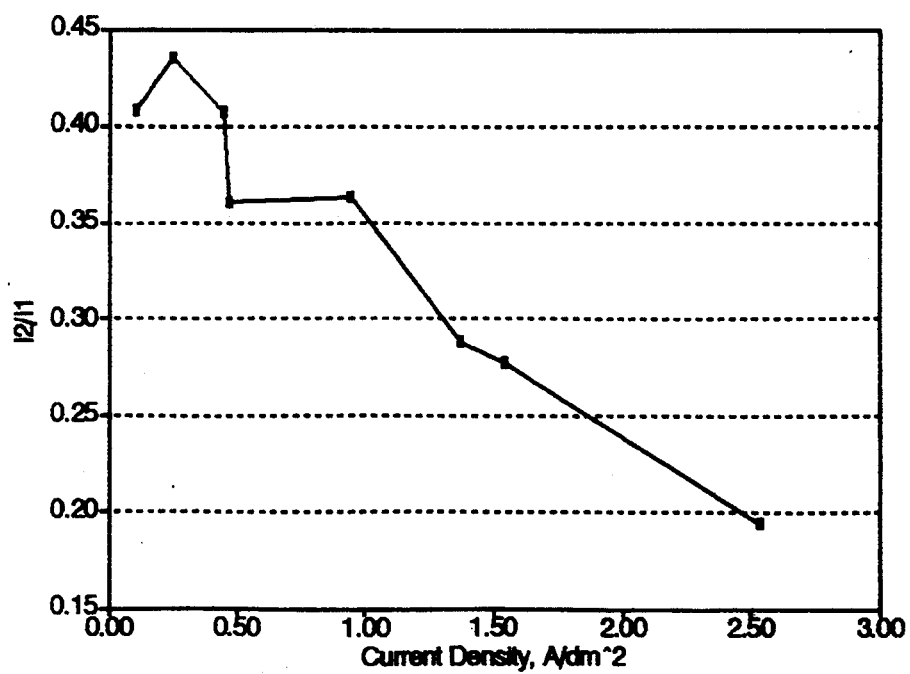
FIG. 7 is a graphic representation of the functional relationship between throwing power, expressed as the ratio of electrode currents, and current density for a two-electrode probe with circulating solution.

In Example 2, similar tests were conducted with a two-electrode probe. The first series of measurements, whose results are plotted in FIG. 6, was carried out in a still solution. In the second series (see FIG. 7), the same solution was circulated during electrolysis through the probe at the speed of 0.11 m/sec while the measurements were being taken. These results are strikingly different, showing a sharp decline in the secondary current distribution uniformity at higher current densities compared to a rise in the unagitated, or still, bath. This test demonstrated the importance of agitation as a process variable and the need for its evaluation in processing uniformity tests.

SUMMARY, RAMIFICATIONS, AND SCOPE

Accordingly, it will be apparent to the skilled artisan that the multipurpose electrolytic meter of this invention can be used to measure processing uniformity and related processing parameters easily and conveniently directly in a process tank, while the tank is in operation.

The main advantage distinguishing my method and apparatus from the prior art is that both the secondary current distribution and the metal distribution for a particular probe geometry are independent of the probe position in the tank and its proximity to the counterelectrode. Consequently, any changes in the metal and current distribution reflect changes in the electrolyte or the processing conditions, making it possible for the first time to compare the performance of different electrolytes in terms of their processing uniformity. The geometry of the probe, with electrodes arranged at various distances from the body opening, makes it possible to measure the variation of processing rate with the cavity depth and, therefore, to use test results for predicting processing uniformity for real objects, for example, blind vias in printed circuit boards. It also allows quantification of the effects, which solution movement has on the processing uniformity. Another advantage is the ability to conduct measurements quickly and directly in a process tank using the existing counterelectrode and current source, with a relatively simple instrument.

In the method of this invention, the parameters for an individual bath are determined and calculated as described hereinabove, and the electrode measurements calibrated in conformance with those calculations. The bath is then operated under control of the desired values as determined by the probe assembly described herein.

In another application of the utility of this invention, bath parameters are determined as described hereinabove, and the bath operated with feedback controls driven by the probe assembly. Thus, if a given throwing power is desired, bath controls can be set to respond to signals received from the probe, based on the calculated values appropriate for that parameter, if the throwing power decreases, a controller linked with that aspect of the apparatus can be programmed then to make a chemical addition. As the particular parameter approaches its optimum value as determined by the probe of this invention, the programmed control function would decrease its operation until the system is again functioning substantially in the middle of the desired range. In this fashion, by way of illustration, an entire plating line can be automated, the various desired values being controlled by input from the multipurpose electrolytic meter of this invention. The control mechanisms and programming for their function are well known to those skilled in the art, and not further described herein, forming no part of this invention as such.

Although the description above contains many specificities, these should not be construed as limiting the scope of the invention but as merely providing illustrations of some of the presently preferred embodiments of this invention. For example, the probe may have a different cavity configuration, more than one free opening, alternate electrode arrangements, etc.

Thus the scope of the invention should be determined by the appended claims and their legal equivalents, rather than by the examples given.

I claim:

1. An apparatus for measuring the operating parameters of an electrochemical processing solution, comprising:
   (a) a plurality of electrodes,
   (b) a nonconductive rigid enclosure provided with a single opening and adapted to be immersed in said process solution, said electrodes being mounted inside said enclosure at various distances from said opening,
   (c) means for delivering current to said electrodes, with all said electrodes being adapted to be connected during testing to the same pole of said means for delivering current, while the opposite pole of said means being connected to a counter-electrode located outside said enclosure and adapted to be immersed in said process solution,
   (d) means for measuring the separate current flowing to each of said electrodes, thereby providing the opportunity to measure throwing power and operating current density range of said solution substantially independently of the position of said enclosure in said process solution during measurements.

2. The apparatus of claim 1 wherein said electrodes are removably mounted inside said enclosure, thereby providing the opportunity to measure additionally the electrochemical efficiency of said solution.

3. The apparatus of claim 2 wherein said enclosure has an elongated shape with two opposite ends, said opening being located at one of said ends.

4. The apparatus of claim 1 wherein said electrodes are identical in shape and size.

5. The apparatus of claim 4 wherein the distance between any two adjacent said electrodes is equal to that between said opening and the electrode nearest to it.

* * * * *